(12) United States Patent
Wycoff

(10) Patent No.: US 8,673,373 B2
(45) Date of Patent: Mar. 18, 2014

(54) HOMEOPATHIC FORMULATIONS FOR TREATMENT OF HERPES VIRUS SYMPTOMS

(75) Inventor: Jeffrey Wycoff, Boulder, CO (US)

(73) Assignee: Paradigm, Inc., Longmont, CO (US)

( * ) Notice: Subject to any disclaimer, the term of this patent is extended or adjusted under 35 U.S.C. 154(b) by 0 days.

(21) Appl. No.: 13/441,357

(22) Filed: Apr. 6, 2012

(65) Prior Publication Data

US 2012/0195970 A1 Aug. 2, 2012

Related U.S. Application Data

(63) Continuation-in-part of application No. 12/658,993, filed on Feb. 17, 2010, now Pat. No. 8,389,025, which is a continuation of application No. 12/002,042, filed on Dec. 14, 2007, now abandoned.

(60) Provisional application No. 60/875,018, filed on Dec. 15, 2006.

(51) Int. Cl.
*A61K 36/00* (2006.01)
*A61K 33/22* (2006.01)
*A61K 33/14* (2006.01)

(52) U.S. Cl.
USPC .......................... 424/725; 424/658; 424/680

(58) Field of Classification Search
None
See application file for complete search history.

(56) References Cited

U.S. PATENT DOCUMENTS

| | | | |
|---|---|---|---|
| 6,248,307 | B1 | 6/2001 | Borneman et al. |
| 2003/0003482 | A1 | 1/2003 | Halle et al. |
| 2005/0129789 | A1 | 6/2005 | Shirota |
| 2005/0255166 | A1 | 11/2005 | Moloney |

FOREIGN PATENT DOCUMENTS

| | | |
|---|---|---|
| CN | 1342491 | 4/2002 |
| RU | 2001402 | 10/1993 |

OTHER PUBLICATIONS

Ernst, is homeopathy a clinically valuable approach? Trends in pharmacological sciences 26 911): 657-548, 2005.*
Kleijnen et al, Clinical trials of homoeopathy, BMJ 302: 316-323, 1991.*
Weissmann, Homeopathy: Holmes, Hogwarts, and the price of Wales, The FASEB Journal 20: 1755-1757, 2006.*
Ernst et al, Efficacy of homeopathic Arnica, Arch Surg 133: 1187-1190, 1998.*
Ernst, A systematic review of systematic reviews of homeopathy, Br J Clin Pharmacol 54: 577-582, 2002.*
U.S. Appl. No. 12/658,993, filed Feb. 17, 2010.
U.S. Appl. No. 12/002,042, filed Dec. 14, 2007.
Provisional U.S. Appl. No. 60/875,018, filed Dec. 15, 2006.
Ernst, et al. Efficacy of Homeopathic Arnica. Arch Surg, vol. 133, pp. 1187-1190, 1998.
Ernst. A Systematic review of Systematic Reviews of Homeopathy. Br J Clin Pharmacol, vol. 54, pp. 577-582, 2002.
Ernst. Is Homeopathy a Clinically Valuable Approach? Trends in Pharmacological Sciences, vol. 26, No. 11, Nov. 2005, pp. 547-548.
Kleijnen et al. Clinical Trials of Homeopathy. BMJ, vol. 302, pp. 316-323, 1991.
McKeon. Herbal Management of Diabetic Leg Ulcers. Australian Journal of Medical Herbalism, vol. 6, No. 4, p. 99, 1994.
Weissmann. Homeopathy: Holmes, Hogwarts, and the Prince of Wales. The FACEB Journal, vol. 20, pp. 1755-1757, 2006.

* cited by examiner

*Primary Examiner* — Qiuwen Mi
(74) *Attorney, Agent, or Firm* — Craig R. Miles; CR Miles, P.C.

(57) ABSTRACT

Compositions and methods of preparing and using such compositions to treat the symptoms of herpes virus.

9 Claims, 7 Drawing Sheets

| MATERIAL | POTENCY DESIGNATION |
|---|---|
| Rhus toxicondendron | between about 6x and about 200c HPUS |
| Ranunculus bulbosus | between about 3x and about 200c HPUS |
| Phytolacca decandra | between about 3x and about 200c HPUS |
| Crab Apple | between about 3x and about 200c HPUS |
| Natrum muriaticum | between about 3x and about 200c HPUS |
| Borax | between about 1x and about 200c HPUS |

FIGURE 1

| MATERIAL | POTENCY DESIGNATION | |
|---|---|---|
| Rhus toxicondendron | 30x | HPUS |
| Ranunculus bulbosus | 12x | HPUS |
| Phytolacca decandra | 3x | HPUS |
| Crab Apple | 5x | HPUS |
| Natrum muriaticum | 30x | HPUS |
| Borax | 1x | HPUS |

FIGURE 2

| MATERIAL | POTENCY DESIGNATION | |
|---|---|---|
| Rhus toxicondendron | 30x | HPUS |
| Ranunculus bulbosus | 12x | HPUS |
| Phytolacca decandra | 3x | HPUS |
| Crab Apple | 1x | HPUS |
| Succinic acid | 15 milligrams (mg) | |

FIGURE 3

| MATERIAL | POTENCY DESIGNATION | |
|---|---|---|
| Rhus toxicondendron | 30x | HPUS |
| Ranunculus bulbosus | 12x | HPUS |
| Phytolaccca decandra | 3x | HPUS |
| Crab Apple | 1x | HPUS |
| Natrum muriaticum | 30x | HPUS |
| Borax | 1x | HPUS |

FIGURE 4

| MATERIAL | POTENCY DESIGNATION | |
|---|---|---|
| Mezereum | 12x | HPUS |
| Phytolacca decandra | 12x | HPUS |
| Ranunculus bulbosus | 12x | HPUS |
| Rhus toxicodendron | 12x | HPUS |
| Sepia | 30x | HPUS |
| Natrum Muriaticum | 12x | HPUS |
| Clematix | 12x | HPUS |
| Influenzinum | 18x | HPUS |

FIGURE 5

| MATERIAL | POTENCY DESIGNATION | |
|---|---|---|
| Mezereum | 12x | HPUS |
| Phytolacca decandra | 12x | HPUS |
| Ranunculus bulbosus | 12x | HPUS |
| Rhus toxicodendron | 12x | HPUS |
| Natrum Muriaticum | 12x | HPUS |
| Clematix | 12x | HPUS |
| Influenzinum | 18x | HPUS |

FIGURE 6

| MATERIAL | POTENCY DESIGNATION | |
|---|---|---|
| Mezereum | 12x | HPUS |
| Phytolacca decandra | 12x | HPUS |
| Ranunculus bulbosus | 12x | HPUS |
| Rhus toxicodendron | 12x | HPUS |
| Sepia | 30x | HPUS |
| Natrum Muriaticum | 30x | HPUS |
| Clematis erecta | 12x | HPUS |
| Anatherum muricatum | 12x | HPUS |
| Thuja occidentalis | 12x | HPUS |

FIGURE 7

HOMEOPATHIC FORMULATIONS FOR TREATMENT OF HERPES VIRUS SYMPTOMS

This United States Patent Application is a continuation-in-part of U.S. patent application Ser. No. 12/658,993, filed Feb. 17, 2010, which is a continuation of U.S. patent application Ser. No. 12/002,042, filed Dec. 14, 2007, and claims the benefit of U.S. Provisional Patent Application No. 60/875,018 filed Dec. 15, 2006, each hereby incorporated by reference herein.

I. BACKGROUND

Compositions and methods of preparing and using such compositions to treat the symptoms of herpes virus.

The herpes simplex virus (HSV) is a virus that manifests itself in two common viral infections, each marked by painful, watery blisters in the skin or mucous membranes (such as the mouth or lips) or on the genitals. The disease is contagious, particularly during an outbreak, and is incurable with present technology. An infection on the lips is commonly known as a "cold sore" or "fever blister". These are sometimes confused with canker sores or aphthous ulcers, which have a similar appearance; these appear inside the mouth and are not caused by the herpes simplex virus. When asymptomatic, HSV lies dormant in the bodies of the nerve cells, replicating within the axons towards the skin during an outbreak. When the outbreak has passed, the virus 'dies back' along the nerve until it is only present in the nerve body. The dormancy of the virus within the nerve bodies contributes to the difficulty of treatment.

There is currently no cure for HSV. Treatment in the form of antiviral medications such as Acyclovir (trade name Zovirax), Famciclovir, pancyclovir, valacyclovir, or the like, which reduce the duration of symptoms and accelerates healing are available. Treatment typically begins at the first symptoms of an outbreak.

Another option is the use of daily suppressive therapy, in which antivirals are taken every day over the course of years. Suppressive therapy may reduce frequency of symptoms and recurrence of outbreaks. In addition, suppressive therapy reduces subclinical shedding, lowering the risk of transmission through sexual contact or kissing.

A substantial problem with taking antiviral medications can be side effects such as confusion, hallucinations, increased thirst, redness, blistering, peeling or loosening of the skin, including inside the mouth, reduced amount of urine passed, seizures, skin rash or hives, stomach pain, tremor, unusual weakness or tiredness, diarrhea, dizziness, headache, increased sensitivity to the sun, loss of appetite, nausea, or vomiting.

Due to the various adverse effects associated with antiviral drug therapy, certain herbal remedies have been utilized to alleviate herpes virus symptoms such as pau d'arco, echinacea, burdock root, nettle, chamomile, St. John's wort, skullcap, passionflower, goldenseal, comfrey leaf, calendula, or chapparal leaves or combinations thereof. Homeopathic remedies have also been utilized to alleviate herpes virus symptoms such as *Natrum Muriaticum, Rhus toxicodendron, Mercurius, Sepia*, or combinations thereof.

Homeopathic products useful in treating herpes virus symptoms are described in the Homeopathic Pharmacopeia of the United States (HPUS). There are benefits to utilizing herbal and homeopathic remedies because they appear to reduce certain herpes virus symptoms and because the compliance rate can be high while the rate of side effects can be low.

Despite advances in the art of herbal and homeopathic remedies, there remains a need for additional compositions, formulations, mixtures, potency dilution admixtures, or the like and methods of preparing and using such compositions, formulations, potency dilution admixtures, or the like to treat the symptoms of herpes virus which as compared to conventional compositions, formulations, mixtures, potency dilution admixtures provide alternative treatment with respect to the active ingredient or manner of delivery thereof or reduce to a greater degree herpes virus symptoms.

II. SUMMARY OF THE INVENTION

Accordingly, a broad object of the invention can be to provide compositions, formulations, and potency dilution admixtures for the treatment of herpes virus symptoms.

Another broad object of the invention can be to provide improved methods for preparing formulations, particularly with respect to oral and topical dosage forms, useful in treating herpes virus symptoms.

Another broad object of the invention can be to provide methods of treating herpes virus symptoms such as treatment preventing or providing a reduction in the frequency or severity of at least one such symptom, or both the frequency or severity of at least one such symptom, or otherwise mitigating such symptoms.

Another broad object of the invention can be to provide methods of preparing an oral dosage form for the treatment of herpes virus symptoms. Such dosage forms may be prepared by admixing or combining the requisite amounts of homeopathic or herbal components, or both, together with any pharmaceutical excipients, and dividing the mixture into unit doses containing an appropriate amount of the admixture or combination to treat herpes virus symptoms when administered to a person whether in solid unit dosage or topical forms such as creams or liquids.

Another broad object of the invention can be to provide a method of treating herpes virus symptoms by administering a unit dose of the homeopathic components herein described orally to a person as a treatment for herpes virus symptoms.

Another broad object of the invention can be to provide a method of treating herpes virus symptoms by administering a unit dose of the homeopathic components herein described topically to a person as a treatment for herpes virus symptoms.

Naturally, further objects of the invention are disclosed throughout other areas of the specification, drawings, photographs, and claims.

III. A BRIEF DESCRIPTION OF THE DRAWINGS

FIG. 1 is a particular embodiment of the inventive compositions encompassed by the invention.

FIG. 2 is a particular embodiment of the inventive compositions encompassed by the invention.

FIG. 3 is a particular embodiment of the inventive compositions encompassed by the invention.

FIG. 4 is a particular embodiment of the inventive compositions encompassed by the invention.

FIG. 5 is a particular embodiment of the inventive compositions encompassed by the invention.

FIG. 6 is a particular embodiment of the inventive compositions encompassed by the invention.

FIG. 7 is a particular embodiment of the inventive compositions encompassed by the invention.

IV. DETAILED DESCRIPTION OF THE PREFERRED EMBODIMENTS

Compositions and methods of preparing and using such compositions to treat the symptoms of herpes virus.

Compositions can be admixtures of components or ingredients, or prepared by the process of homeopathic drug preparation. Homeopathic drug preparation is based on the concept of potentization or potentiation. Homeopathy relies on the administration of successively more diluted formulations of key homeopathic components to affect a desired response. The manufacturing process underlying this philosophy, therefore, requires the preparation of dilutions that represent very small fractions of the original base product's composition. Products available commercially or prepared by homeopathic physicians and pharmacists may be combined with alcohol, distilled water, or lactose as their dilution matrix. Mother tincture (also referred to as "Ø") typically refers to a crude homeopathic compound that is triturated in alcohol.

Potency designations refer to the dilution of the mother mix. One part drug mixed with 9 parts dilution matrix is designated a 1× potency. A potency designation of 10× (or 1c) is composed of 1 part mother tincture diluted in 99 parts of a selected diluent. A potency designation 1m is 1 part mother tincture mixed in 999 parts of selected dilution. A potency of 2× is 1 part 1× potency and 9 parts of dilution. Low potency examples are 1×, 6×, 6c. Examples of medium potency include 30× and 30c. High potency examples are 200c, 1m, 20m.

"HPUS" as referred to herein means a material prepared in accordance to the specifications of the Homeopathic Pharmacopoeia of the United States, hereby incorporated by reference herein. The Federal Food, Drug and Cosmetic Act recognizes as official the drugs and standards in the Homeopathic Pharmacopeia of the United States and it supplements.

The term "composition" as used herein refers to any single material or combination, mixture, or admixture of materials, or admixture of dilution potencies, or mixture of diluted materials (whether diluted as mixtures of active substances with excipients as solids or diluted as mixtures of active substances with excipients as liquids), or the like, an amount of which can provide a dose, or an amount of which can be divided into a plurality of doses, or can be divided into amounts a plurality of which can be combined to provide a dose (such as two or more capsules, tablets, drops, or measures of a powder, or the like). A "dose" upon administration to a patient affects herpes virus symptoms, as above-described. The term "dosage form" as used herein refers to a dose established in any manner capable of delivery to a patient and without limitation includes solid dosage forms such as an amount powder, an amount of effervescent powder, an amount of the composition pressed or compacted to provide a solid typically configured to be swallowed such as a tablet, or a plurality of tablets, or a number of tablets which individually or in combination provide a dose, a caplet, a capsule which contains an amount of the composition, and further includes liquid dosage forms such as an amount of liquid, a drop of liquid, a plurality of drops of liquid, or a number of drops of liquid which individually or in combination allow delivery of a dose. The term oral dosage form whether a liquid oral dosage form or a solid oral dosage form provides delivery of a dose by introduction of the dosage form(s) whether liquid or solid into the mouth. The term "tablet" as used herein refers to an amount of the composition pressed or compacted or otherwise established in a solid form (including without limitation the active substances applied as liquids to pressed or compacted amounts of excipients in solid form) configured to be taken orally.

As to certain embodiments, a dosage form can include a composition which includes in sufficient amount an admixture of ingredients or homeopathic formulation of *Rhus toxicondendron, Ranunculus bulbosus, Phytolacca decandra*, and *Malus pumila* for treatment of herpes virus symptoms in a patient. Other dosage forms can further include one or more components in an amount, or as homeopathic preparations, of *Natrum muriacticum, Succinic acid, Borax*, or as to other dosage forms one or both of *Natrum muriacticum* and *Borax* can be included.

Now referring primarily to FIG. 1 and Table 1, certain homoeopathic embodiments of the composition can provide a potency of *Rhus toxicondendron* of between about 6×HPUS and about 200c HPUS, a potency of *Ranunculus bulbosus* of between about 3×HPUS and about 200c HPUS, a potency of *Phytolacca decandra* of between about 3×HPUS and about 200c HPUS, a potency of *Malus pumila* of between 1× and about 200c (or an equivalent molar amount of each component). The dosage form can further include a potency of *Natrum muriacticum* of between about 3×HPUS and about 200c HPUS or can include a potency of *Borax* of between about 6×HPUS and about 200c HPUS, or can include both a potency of *Natrum muriacticum* of between about 3×HPUS and about 200c HPUS and a potency of *Borax* of between about 6×HPUS and about 200c HPUS (or the equivalent molar amount of each).

As to those embodiments of the invention which provide an oral solid dosage form, the oral solid dosage form retains the original HPUS strength of dilution as above described or as set out in FIGS. 1-7 or Tables 1-7 below depending on the embodiment. Particular embodiments of an oral solid dosage form can be a tablet dosage form which provides an admixture of an amount or potency of *Rhus toxicondendron, Ranunculus bulbosus, Phytolacca decandra*, and *Malus pumila*. An amount or potency of *Natrum muriaticum* or an amount of *Borax* (or an amount of both) can be admixed.

Now referring primarily to FIG. 2 and Table 2, as but one example, a preferred oral dosage form can comprise a tablet which provides a potency of *Rhus toxicondendron* (Poison Ivy) 30×HPUS, *Ranunculus bulbosus* (Buttercup) 12×, *Phytolacca decandra* (Pokeroot) 3×, *Malus pumila* (Crab Apple) 5×, *Natrum muriaticum* (Sodium Chloride) 30×, and *Borax* (Sodium Borate) 1× (or other formulation as described herein) and further including excipients admixed providing an amount of Magnesium Stearate, Microcrystalline Cellulose, and Sucrose which can be divided and compressed to form a tablet of a configuration and weight suitable for oral administration.

A preferred tablet dosage form including the active ingredients and inactive ingredients as above-described can provide a circular geometry with a diameter of between about 9.0 millimeters to about 10.0 millimeters and a thickness of between about 4.00 millimeters to about 5.00 millimeters providing a weight of between about 0.290 and about 0.310 grams. The tablet can have a hardness of between about 2.5 Kp and about 5.0 Kp with a friability of less than about 1 percent which disintegrates in less than 30 minutes. This particular embodiment of an oral solid dosage form is not intended to be limiting with respect to the numerous and varied oral solid dosage forms which can provide a dose for the treatment of symptoms of herpes virus, but rather it is intended to provide a person of ordinary skill in the homeopathic field a description sufficient to make and use the numerous and varied embodiments of the invention encompassed by this description.

An example of a dose for the treatment of cold sore or oral herpes virus symptoms and a an example of a method of treating herpes virus symptoms (including treatment with the particular oral dosage form of a tablet described above) can include chewing three tablets at the first sign of herpes virus symptoms such as burning or itching, and then chewing three tablets three times daily until symptoms disappear. A non-limiting example of a dose for the treatment of genital herpes symptoms and a non-limiting example of a method of treating genital herpes symptoms (including treatment with the particular oral dosage form of a tablet described above) can include chewing between 3 and 5 tablets 3 times daily for prevention of outbreaks and at the first sign of herpes virus symptoms such as burning or itching, and then chewing 3 tablets 3 times daily until symptoms disappear.

A method of preparing a dosage form of a particular homeopathic composition can include the steps of admixing a sufficient amount or potencies of *Rhus toxicondendron, Ranunculus bulbosus, Phytolacca decandra*; and *Malus pumila* (or other formulation as described herein) to establish a mixture of amounts or potencies and dividing the mixture to provide a plurality of a dosage form. The method can further comprise the step of admixing a sufficient amount or potency of at least one of *Natrum muriacticum* or *Borax* (or both). The method can further include the step of admixing an amount of excipients such as Magnesium Stearate, Microcrystalline Cellulose, and sucrose in various combinations and permutations. This example is intended to provide a person of ordinary skill in the art a description sufficient to make and use the numerous embodiments of the invention as herein described.

Now referring primarily to Table 2 and FIG. 2, one example of a method of preparing a dosage form of a homeopathic composition can include the steps of admixing an amount of a mother trituration *Rhus toxicondendron* 27×HPUS, *Ranunculus bulbosus* 9×HPUS, *Malus pumila* 2×, and *Natrum muriaticum* 27× of about 0.67 percent by weight (weight of a component divided by the total weight of the final prepared mixture) with an amount of microcrystalline cellulose (such as Emcocel 90M) about 6.0 percent by weight in a blender (such as a V-blender or tumble blender) for about 30 minutes. To this mixture, admix an amount of compressible sucrose (such as Easy-Fond) about 76.5 percent by weight, an amount of microcrystalline cellulose about 11.9% by weight, an amount of *Borax* about 1.67% by weight, and an amount of *Phytolacca Decandra* 2× (yield from first tituration of *Phytolacca Decandra* 1× (about 475 grams) admixed with Lactose, Anhydrous, USP (4,750 grams)) about 1.67 percent by weight in a tumble blender for about 55 minutes. To this mixture, admix magnesium stearate about 2.0% by weight in a tumble blender for about 5 minutes. Screen the finished mixture through a 20 mesh screen and transfer to a vessel for storage. Subsequently, compress into a tablet dosage form of the above-described configuration and dose or the other chewable configuration or dose depending on the formulation.

As to those embodiments of the invention which provide a topical dosage form (such as an amount of a liquid or an amount of a cream) the original HPUS strength of dilution as above described or as set out in FIGS. 1-7 or Tables 1-7 below can be maintained. As to particular embodiments of a topical dosage form, a cream or a liquid can provide an admixture or potency of *Rhus toxicondendron, Ranunculus bulbosus, Phytolacca decandra*, and *Malus pumila* to which an amount of *Natrum muriaticum* or an amount of *Borax* (or an amount of both) can be admixed. Now referring primarily to FIG. 4 and Table 4 as but one non-limiting example, a preferred topical dosage form can comprise a cream or a liquid which provides *Rhus toxicondendron* (Poison Ivy) 30×HPUS, *Ranunculus bulbosus* (Buttercup) 12×, *Phytolacca decandra* (Pokeroot) 3×, *Malus pumila* (Crab Apple) 1×, *Natrum muriaticum* (Sodium Chloride) 30×, and *Borax* (Sodium Borate) 1× admixed into an amount of lactose, magnesium stearate, microcrystalline cellulose to form a cream for topical administration or an amount of distilled water to provide a liquid for topical administration.

Now referring to FIG. 1 and Table 1, a first exemplary embodiment of the inventive compositions to alleviate or reduce symptoms of herpes virus, can include in an oral dosage form (such as a tablet or capsule) or a topical dosage form having the following formulation:

TABLE 1

| MATERIAL | POTENCY DESIGNATION |
| --- | --- |
| *Rhus toxicondendron* | between about 6x and about 200 c HPUS |
| *Ranunculus bulbosus* | between about 3x and about 200 c HPUS |
| *Phytolacca decandra* | between about 3x and about 200 c HPUS |
| Crab Apple | between about 3x and about 200 c HPUS |
| Natrum muriaticum | between about 3x and about 200 c HPUS |
| Borax | between about 1x and about 200 c HPUS |

Now referring to FIG. 2 and Table 2, a second exemplary embodiment of the inventive compositions to alleviate or reduce symptoms of herpes virus, can include in an oral dosage form (such as a tablet or capsule) the following formulation:

TABLE 2

| MATERIAL | POTENCY DESIGNATION |
| --- | --- |
| *Rhus toxicondendron* | 30x HPUS |
| *Ranunculus bulbosus* | 12x HPUS |
| *Phytolacca decandra* | 3x HPUS |
| Crab Apple | 5x HPUS |
| Natrum muriaticum | 30x HPUS |
| Borax | 1x HPUS |

Now referring to FIG. 3 and Table 3, a third exemplary embodiment of the inventive compositions to alleviate or reduce symptoms of herpes virus, can include in an oral dosage form (such as a tablet or capsule) the following formulation:

TABLE 3

| MATERIAL | POTENCY DESIGNATION |
| --- | --- |
| *Rhus toxicondendron* | 30x HPUS |
| *Ranunculus bulbosus* | 12x HPUS |
| *Phytolacca decandra* | 3x HPUS |
| Crab Apple | 1x HPUS |
| Succinic acid | 15 milligrams (mg) |

Now referring to FIG. 4 and Table 4, a fourth exemplary embodiment of the inventive compositions to alleviate or reduce symptoms of herpes virus, can include in a topical dosage form such as an ointment, cream, or liquid the following formulation:

TABLE 4

| MATERIAL | POTENCY DESIGNATION |
|---|---|
| *Rhus toxicondendron* | 30x HPUS |
| *Ranunculus bulbosus* | 12x HPUS |
| *Phytolaccca decandra* | 3x HPUS |
| Crab Apple | 1x HPUS |
| Natrum muriaticum | 30x HPUS |
| Borax | 1x HPUS |

Now referring to FIG. 5 and Table 5, a fifth exemplary embodiment of the inventive compositions to alleviate or reduce symptoms of herpes virus, can include in a topical dosage form such as an ointment or a cream the following formulation:

TABLE 5

| MATERIAL | POTENCY DESIGNATION |
|---|---|
| *Mezereum* | 12x HPUS |
| *Phytolacca decandra* | 12x HPUS |
| *Ranunculus bulbosus* | 12x HPUS |
| *Rhus toxicodendron* | 12x HPUS |
| *Sepia* | 30x HPUS |
| Natrum Muriaticum | 12x HPUS |
| Clematix | 12x HPUS |
| Influenzinum | 18x HPUS |

Now referring to FIG. 6 and Table 6, a fifth exemplary embodiment of the inventive compositions to alleviate or reduce symptoms of herpes virus, can include in a topical dosage form such as an ointment or a cream the following formulation:

TABLE 6

| MATERIAL | POTENCY DESIGNATION |
|---|---|
| *Mezereum* | 12x HPUS |
| *Phytolacca decandra* | 12x HPUS |
| *Ranunculus bulbosus* | 12x HPUS |
| *Rhus toxicodendron* | 12x HPUS |
| Natrum Muriaticum | 12x HPUS |
| Clematix | 12x HPUS |
| Influenzinum | 18x HPUS |

As to other embodiments, a dosage form can include a composition which includes in sufficient amount an admixture of ingredients or homeopathic formulation of *Mezereum, Phytolacca decandra, Ranunculus bulbosus, Rhus toxicodendron* for treatment of herpes virus symptoms in a patient. Other dosage forms can further include one or more components in an amount, or as homeopathic preparations, of *Natrum muriacticum, Sepia*, an amount of *Clematix*, an amount of *Influenzinum*, an amount of *Anatherum muicatum*, or *Thuja occidentalis*.

Now referring to Table 7, a seventh exemplary embodiment of the inventive compositions to alleviate or reduce symptoms of herpes virus, can include an oral dosage form (such as a tablet or capsule) the following formulation:

TABLE 7

| MATERIAL | POTENCY DESIGNATION |
|---|---|
| *Mezereum* | between about 2x and about 400x HPUS |
| *Phytolacca decandra* | between about 2x and about 400x HPUS |
| *Ranunculus bulbosus* | between about 2x and about 400x HPUS |
| *Rhus toxicodendron* | between about 2x and about 400x HPUS |
| *Sepia* | between about 2x and about 400x HPUS |
| Natrum Muriaticum | between about 2x and about 400x HPUS |
| *Clematis erecta* | between about 2x and about 400x HPUS |
| *Anatherum muricatum* | between about 2x and about 400x HPUS |
| *Thuja occidentalis* | between about 2x and about 400x HPUS |

Now referring to Table 8, a seventh exemplary embodiment of the inventive compositions to alleviate or reduce symptoms of herpes virus, can include an oral dosage form (such as a tablet or capsule) the following formulation:

TABLE 8

| MATERIAL | POTENCY DESIGNATION |
|---|---|
| *Mezereum* | between about 2x and about 12x HPUS |
| *Phytolacca decandra* | between about 2x and about 12x HPUS |
| *Ranunculus bulbosus* | between about 2x and about 12x HPUS |
| *Rhus toxicodendron* | between about 2x and about 12x HPUS |
| *Sepia* | between about 2x and about 12x HPUS |
| Natrum Muriaticum | between about 2x and about 12x HPUS |
| *Clematis erecta* | between about 2x and about 12x HPUS |
| *Anatherum muricatum* | between about 2x and about 12x HPUS |
| *Thuja occidentalis* | between about 2x and about 12x HPUS |

Now referring to Table 9 and FIG. 7, a seventh exemplary embodiment of the inventive compositions to alleviate or reduce symptoms of herpes virus, can include or consist of an oral dosage form (such as a tablet or capsule) the following formulation:

TABLE 9

| MATERIAL | POTENCY DESIGNATION |
|---|---|
| *Mezereum* | about 12x HPUS |
| *Phytolacca decandra* | about 12x HPUS |
| *Ranunculus bulbosus* | about 12x HPUS |
| *Rhus toxicodendron* | about 12x HPUS |
| *Sepia* | about 12x HPUS |
| Natrum Muriaticum | about 12x HPUS |
| *Clematis erecta* | about 12x HPUS |
| *Anatherum muricatum* | about 12x HPUS |
| *Thuja occidentalis* | about 12x HPUS |

Depending on the dosage form one or more of the following excipients can be admixed to the active ingredients to produce a dosage form for a particular route of administration such as a tablet, cream, gel, ointment, or liquid.
Excipient.
Lactose
Microcyrstalline cellulose
Magnesium Stearate
Calcium phosphate
PEG8000
Silicon dioxide
Glycerol monostearate
Water The HPUS describes the manner preparing homeopathic formulations, the following intended to be a sufficient portion of the description to make the tinctures and potencies for the various homeopathic formulations, described herein.

*Rhus toxicondendron* is a deciduous shrub, with reddish, branching stem, 1 to 3 feet high, or climbing by rootlets, or ascending trees, in which latter case it becomes *Rhus radicans*. The leaves are alternate, ternate, the lateral leaflets unequal at the base and sessile, the terminal one larger at the end of a prolongation of the common petiole (cauline differing from the radical), rhombic-ovate pointed, variously notched or entire, cut-lobed, downy beneath, and thin. The small greenish-white flowers are polygamous and appear in June in loose and slender axillary panicles. The whole plant has a resinous, milky, acrid juice, staining black and extremely poisonous. A tincture can be made from a moist magma of fresh leaves containing solids of about 100 grams and plant moisture of about 200 cc transferred to about 824 cc alcohol to make about 1000 cc of tincture. Dilutions of 2× and higher, can be made by dilution with dispensing alcohol.

*Ranunculus bulbosus* is a deciduous, perennial herb, the root a fleshy, round-ish, depressed corm, about 1 inch in diameter, sending out rootlets underneath. The several stems are about 1 foot high, erect, round, branched, hairy, without runners. The radical leaves are ternate, the lateral divisions sessile, the terminal petiolate, three-parted, wedge-shaped, cleft and dentate. The numerous glossy-yellow flowers, more than an inch broad, appear from April to August, are solitary, terminal, onangular, furrowed, bristly peduncles. The whole fresh plant, gathered during flowering. A tincture of *Ranunculus bulbosus* can be prepared using moist magma of the whole fresh plant containing solids of about 100 grams and plant moisture of about 300 cc in about 730 cc to make about 1000 cc of tincture. Dilutions can be made 2× to contain one part tincture, two parts distilled water, seven parts alcohol with 3× and higher with dispensing alcohol.

*Phytolacca decandra* is commonly referred to as poke. A tall, stout, perennial herb, with large, fleshy, branching root, often 4 to 6 inches in diameter, easily cut or broken, with a very thin, brownish bark, internally marked with thick concentric rings. The annual stem, 4 to 10 feet high, 1 inch in diameter, is erect, cylindrical, hollow, branching, smooth, and of a purplish color when mature. The leaves are large, scattered, petiolate, entire. The white flowers appear from July to September, in terminal racemes, which become lateral and opposite the leaves as the plant grows. The fruit is a dark-purple, juicy berry, ripening in autumn. The root of the plant not too rank in growth can be pulverized and mixed with alcohol. A tincture can be prepared from the moist magma of the root containing solids of about 100 grams and plant moisture of about 400 cc transferred to about 635 cc alcohol, to make about 1000 cc of tincture. Dilutions of 2× to contain one part tincture, three parts distilled water, six parts alcohol; 3× and higher, with dispensing alcohol.

Succinic acid is a solid that forms colorless, odorless crystals. It has a melting point of 185° C. and a boiling point of 235° C. It is a diprotic acid. The anion, succinate, is a component of the citric acid cycle and is capable of donating electrons to the electron transfer chain and with respect to the dosage formulation of Table 3 between about 10 mg and 20 mg can by utilized per dose with a preferred embodiment including about 15 mg per dose.

*Natrum muriaticum* commonly known as sodium chloride or salt. Sodium chloride can be dissolved in hot, boiling water. The mixture is then filtered and crystallized through evaporation. The resulting substance is then dissolved in water and succussed to create the final preparation of between about 3× to about 200c.

*Borax* or sodium borate can be dissolved in hot, boiling water. The mixture is then filtered and crystallized through evaporation. The resulting substance is then dissolved in water and succussed to create the final preparation which can be between about 4× to about 200c.

*Daphne mezereum* (also referred to as *Mezereum*) is a species of Daphne in the flowering plant family Thymelaeaceae. A hardy, deciduous shrub, with a stem to 4 feet high, with smooth, gray bark, easily detachable from the wood, and branches upright, alternate, smooth, tough and pliant. The leaves, 2 inches long, are alternate from the ends of branches, petioled, scattered, lanceolate, entire, very smooth, green, somewhat glaucous beneath. They appear after the flowers, and are soon followed by flower buds of the next season. The fragrant, purple, rose-colored flowers (rarely white) appear from February to April, in lateral clusters on shoots of the preceding year, in axils of fallen leaves, 3 on a stem. The bark, when fresh, has an unpleasant odor, which disappears as the bark dries. The bark of the root is at first sweetish, but afterwards has a highly acrid taste. A tincture can be made from the bark. A moist magma of the bark containing solids of about 100 grams and plant moisture of about 200 cc can be transferred to about 824 cc alcohol to make about 1000 cc of tincture. Dilutions 2× and higher can be made with dispensing alcohol.

*Sepia* is the discharge used by the cuttlefish to disappear from a predator. The composition dosage form prepared in accordance with the HPUS of between about 3× and 400× potency with a preferred embodiment of about 30×.

*Clematix* in a potency of about 6× to about 20× with a preferred embodiment as set forth by Table 3 of about 12×.

Crabapple flowers such as those of *Malus pumila* can be used to prepare a tincture by the Sun Method or the Boiling Method. By way of the Sun Method, 1 part of flower-heads, picked just below the calyx or the flowering spikes, is floated on the surface of 50 parts of water. This is left for 3 hours in full sunshine. The flower-heads are then removed and the water filtered to provide the mother tincture. It is mixed with an equal volume of brandy and vigorously shaken. This is further diluted 1 part in 500 with ethanol (22%) w/w. This final dilution corresponds to the homoeopathic potency of 5×. The Boiling Method can be used to prepare mother tinctures from crabapple flowers. One part flowers can be boiled in 10 parts of water for 30 minutes then allowed to cool. The solution is then decanted and filtered. This mother tincture is mixed with an equal volume of Brandy and vigorously shaken. This is further diluted 1 part in 500 with ethanol (22%) w/w. This final dilution approximates to the homoeopathic potency of 5×.

*Influenzinum* is a homeopathic preparation made from flu viruses. A proprietary preparation for example is produced by Dolisos pharmacy each year using the flu virus strains recommended by the World Health Organization for the year's vaccine production. The composition dosage form prepared can be about 12× and 200c potency.

*Clematis erecta* (also referred to as Virgin's Bower) is perennial, deciduous, climbing plant, with a white, fibrous root. The stem is about 3 feet high, greenish or reddish, nearly smooth. The leaves are large, opposite, with petiolate leaflets five to nine. The flowers, appearing from July to October, are white, in upright, terminal umbels. It climbs by the twisting of the leaf stalks. All parts are extremely acrid, the acridity being diminished by drying. A tincture can be prepared from the fresh leaves and stems shortly before blossoming. *Clematis erecta*, moist magma containing solids of about 100 grams and plant moisture of about 400 cc can be mixed with alcohol, 635 cc, to make to make about 1000 cc of tincture. Dilutions 2× to contain one part tincture, four parts distilled water, five parts alcohol; 3× and higher, with dispensing alcohol.

*Thuja occidentalis* is an evergreen tree, 20 to 50 feet high, with sprays, or branchlets, flat and spreading, dark-green and rather glaucous above, pale beneath, yielding a pungent, aromatic oil. The wood is light and very durable. The leaves are persistent, appressed, imbricated in four rows on the two-edged branchlets; they are of two kinds on alternate or separate branchlets, one form awl-shaped, the other short, squamose, both having a small dorsal gland filled with a thin aromatic turpentine. The flowers appear in May and June, mostly monoecious on different branches in very small, terminal, ovoid catkins. A tincture can be prepared by finely chopping branchlets and transferring the moist magma of about 100 grams of solid and about 135 cc of plant moisture into 885 cc of alcohol, to make about 1000 cc tincture which can be diluted 2× and higher with dispensing alcohol.

*Anatherum muricatum* (also referred to as *Andropogon muricatus*) is a large grass, with a fibrous root. The spikelets are in pairs, the terminal ones in threes, one being complete and awned, the other one or two sterile, awnless. A tincture is prepared from the dried root by dividing the root into fine pieces and subsequently extracting about 100 grams in 1000 cc of alcohol which can then be diluted 2× and higher.

Glycerol Monostearate (CAS#31566-31-1) is a lipophilic non-ionic surfactant utilized as an emulsifier available for example from ScienceLab.com or Acme-Hardesty; PEG8000 polyethylene glycol (CAS#25322-68-3) average molecular weight 8000, Calcium Phosphate (CAS#7757-93-9), Methylcellulose (CAS#9004-65-3), Silicon Dioxide (CAS#7631-86-9) available for example from Post Apple Scientific, North East PA, can be ad mixed with the active ingredients such as in the exemplary formulation as set out in Table 3. However, it is not intended that these excipients be utilized solely with the formulation of Table 3 but can also be used with the varied and numerous formulations described within the ranges indicated whether of the admixture of Table 3 or of Tables 1 or 2.

Microcrystalline Cellulose is an excipient which as the name implies is cellulose obtained from high quality wood pulp used in the formulation of tablets and capsules. It can be used as a binding agent, due to its excellent compression properties. It also has uses as a disintegrant, in order to increase the biological availability of a medicine, and as a lubricant to aid in the tableting procedure. It is also physiologically inert, odorless and tasteless, making it suitable as a diluent in order to fill out a tablet and make a more convenient and accurate dosage form.

Magnesium Stearate, also called octadecanoic acid magnesium salt, is a white substance which is solid at room temperature used as a filling agent in the manufacture of medical tablets and capsules. In this regard, the substance is also useful because it has lubricating properties, preventing ingredients from sticking to manufacturing equipment during the compression of chemical powders into solid tablets.

Sucrose a sugar purified from sugar cane or sugar beets can be used as a base or an inactive ingredient to dilute other materials and compress to form tablets or other solid dosage forms.

Lactose a sugar obtained from milk can be used as a base or an inactive ingredient in either a hydrous or anhydrous form to dilute other materials.

It is not intended that the examples provided above be limiting with respect to the admixture of additional herbal, homeopathic, or excipient components so long as the additional components do not substantially alter the potency designation of the components as above-listed in Tables 2-6 (or the potency designation of particular embodiments of the invention in the ranges indicated in Table 1) in a dose regardless of dosage form. As such, the dosage forms of the invention may also contain pharmaceutical excipients such as fillers, binders, colorants, flavorants, or the like, whether or not specifically listed.

A dosage form by weight can include a substantial amount of pharmaceutical excipients as described above or as to other dosage forms. Regardless of the amount of excipient, the dosage forms of the present invention are prepared by admixing the components together and dividing the mixture into unit doses of desired strength, preferably such that each unit dose provides an effective amount of the components to provide relief from herpes virus symptoms when administered to a person. Due to physical limitations, a unit dose may be subtherapeutic but can be formulated to provide an effective dose when administered in multiple, i.e. two or more, unit doses or dosage forms at a time. The unit dose can be encapsulated or prepared as tablets according to conventional techniques. To prepare the finished dosage form, the herbal or homeopathic components may be admixed with pharmaceutical adjuvants and encapsulated or prepared as tablets or otherwise prepared as known in the art.

The inventive formulations, including, those formulations and potencies set out in Tables 1-6 can be utilized in tablet dosage form to reduce or alleviate symptoms of herpes virus cold sores by taking 3 tablets immediately at the first sign of burning or itching, then 3 tablets three times daily until symptoms disappear.

With respect to symptoms associated with genital herpes, the inventive formulations, including those formulations and potencies set out in Tables 1-9 and FIGS. 1-7 can be utilized in tablet dosage form to reduce, alleviate or prevent symptoms of severe genital herpes sufferers by taking 3 to 5 tablets three times daily. If an outbreak that does not subside within 10 days, consult your doctor. For mild to moderate symptoms of genital herpes, take 3 tablets immediately at the first sign of burning or itching, and then 3 tablets three times daily until symptoms disappear. If symptoms do not subside within 10 days, consult a physician should be consulted.

The inventive formulations, including, those formulations and potencies set out in Tables 1-9 and FIGS. 1-7 can be prepared as a topical ointment or liquid can be utilized by application to the affected area every 2-3 hours or as needed to reduce or alleviate symptoms of herpes virus. If symptoms do not subside within 10 days a physician should be consulted.

As can be easily understood from the foregoing, the basic concepts of the present invention may be embodied in a variety of ways. The invention involves numerous and varied compositions to alleviate herpes virus symptoms.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "homeopathic drug preparation" should be understood to encompass disclosure of the act of "preparing a homeopathic drug"—whether explicitly discussed or not— and, conversely, were there effectively disclosure of the act of "preparing a homeopathic drug", such a disclosure should be understood to encompass disclosure of a "homeopathic drug preparation" and even a "means for preparing a homeopathic drug." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the compositions to treat herpes virus symptoms herein disclosed and described, ii) the related methods of treating herpes virus or herpes symptoms disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Also, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A method of preparing a dosage form comprising:
   mixing a sufficient amount of *Rhus toxicodendron, Ranunculus bulbosus, Phytolacca decandra*, and *Mezereum;*
   dividing said mixture; and
   forming said dosage forms.

2. The method of claim 1, wherein mixing further comprises *Natrum muriacticum*.

3. The method of claim 1, wherein mixing further comprises *Sepia*.

4. The method of claim 1, wherein mixing further comprises *Clematis erecta*.

5. The method of claim 1, wherein mixing further comprises *Anatherum muricatum*.

6. The method of claim 1, wherein mixing further comprises *Thuja occidentalis*.

7. A method of a administering a composition, comprising: orally administering said dosage form of claim 1.

8. The method of claim 4, wherein said dosage form is selected from the group consisting of: an amount powder, an amount of effervescent powder, a tablet, a caplet, a capsule, drops, and combinations thereof.

9. The method of claim 4, wherein said dosage form comprises a tablet and further comprising orally administrating at least one tablet.

* * * * *